US005837273A

United States Patent [19]
Shasha et al.

[11] Patent Number: 5,837,273
[45] Date of Patent: Nov. 17, 1998

[54] METHODS AND COMPOSITIONS OF ADHERENT STARCH GRANULES FOR ENCAPSULATING PEST CONTROL AGENTS

[75] Inventors: Baruch S. Shasha, Peoria; Michael R. McGuire, Metamora, both of Ill.

[73] Assignee: The United States of America as represented by the Secretary of Agriculture, Washington, D.C.

[21] Appl. No.: 730,763

[22] Filed: Jul. 16, 1991

[51] Int. Cl.[6] ........................... A01N 25/12; A01N 25/24

[52] U.S. Cl. ......................... 424/405; 424/407; 424/484; 424/488; 424/489

[58] Field of Search ................................... 424/405, 407, 424/484, 488, 489, 493, 499; 127/65, 71; 435/178; 514/965

[56] References Cited

U.S. PATENT DOCUMENTS

| | | | |
|---|---|---|---|
| 2,876,160 | 3/1959 | Schoch et al. | 514/725 |
| 3,666,557 | 5/1972 | Jensen et al. | 127/32 |
| 3,922,354 | 11/1975 | Galluzzi et al. | 426/96 |
| 4,230,687 | 10/1980 | Sair et al. | 424/485 |
| 4,605,622 | 8/1986 | Hasegawa et al. | 435/178 X |
| 4,701,326 | 10/1987 | Nelsen et al. | 424/408 |
| 4,755,397 | 7/1988 | Eden et al. | 427/213.3 |
| 4,812,445 | 3/1989 | Eden et al. | 514/60 |
| 4,859,377 | 8/1989 | Shasha et al. | 264/4.1 |
| 4,888,171 | 12/1989 | Okonogi et al. | 424/93 R |
| 4,911,952 | 3/1990 | Doane et al. | 427/213.31 |
| 5,051,133 | 9/1991 | Nagai et al. | 536/102 X |
| 5,141,744 | 8/1992 | Chang et al. | 424/93 R |
| 5,183,690 | 2/1993 | Carr et al. | 427/213.31 |

FOREIGN PATENT DOCUMENTS

| | | | |
|---|---|---|---|
| WO85/04074 | 9/1985 | Canada | A01N 25/04 |

OTHER PUBLICATIONS

Koestler, Microencapsulation by Interfacial Polymerization Techniques–Agricultural Applications, pp. 117–132 In Kydonieus (ed.) Controlled Release Technologies: Methods, Theory, and Applications, CRC Press, Boca Raton (1980).

Lance et al., Field–Cage and Laboratory Evaluations of Semiochemical–Based Baits for Managing Western Corn Rootworm Beetles (Coleoptera Chrysomelidae), J. Econ. Entomol. 83: 1085–1090 (1990).

McGuire et al., "Field Evaluation of Granular Starch Formulations of *Bacillus thuringiensis* Against *Ostrinia nubilalis* (Lepidoptera: Pyralidae)," J. Econ. Entomol. 83: 2207–2210 (1990).

McGuire et al., "Evaluation of Starch–Encapsulation for Formulation of Grasshopper (Orthoptera: Acrididae) Entomopoxviruses," J. Econ. Entomol., in press.

Meinke et al., "Pheromone Delivery System: Western Corn Rootworm (Coleoptera Chrysomelidae) Pheromone Encapsulation in a Starch Borate Matrix," J. Econ. Entomol. 82(6): 1830–1835 (1989).

Metcalf et al., "Cinnamyl Alcohol and Analogs as Attractants for Corn Rootworms (Coleoptera: Chrysomeliade)," J. Econ. Entomol. 82(6): 1620–1625 (1989).

Raun et al., "Encapsulation as a Technique for Formulating Microbial and Chemical Insecticides," J. Econ. Entomol. 59(3): 620–622 (1966).

Shasha et al., "Starch–Borate Complexes for EPTC Encapsulation," J. Appl. Polym. Sci., 29: 67–73 (1984).

(List continued on next page.)

*Primary Examiner*—Robert H. Harrison
*Attorney, Agent, or Firm*—M. Howard Silverstein; Curtis P. Ribando; John D. Fado

[57] ABSTRACT

The present invention relates to methods and compositions for encapsulating biologically active agents in starch-based adherent granules. Simple and economic methods have been developed to prepare said adherent granules. Compositions and characteristics of the granules are disclosed, including their capability for sustained release of pest control agents. These methods and compositions are useful in controlling insects and other species of pests having chewing mouth parts and amylase digestive enzymes.

13 Claims, 3 Drawing Sheets

OTHER PUBLICATIONS

Shotwell, "Evaluation of Baits and Bait Ingredients Used in Grasshopper Control," USDA Tech. Bull. 793 (Mar. 1942).

Synek, "Formulation, Development, and Application of an Insecticide Granule," In Kaneko/Akesson (eds.), Pesticide Formulations and Application Systems: Third Symposium, ASTM STP 828, American Society for Testing and Materials, Philadelphia, pp. 123–131 (1983).

Trimnell et al., "Autoencapsulation: A New Method for Entrapping Pesticides Within Starch," J. Contr. Release 7: 25–31 (1988).

Trimnell et al., "Entrapment of herbicides in Starch for Spray Applications," J. Contr. Release 7: 263–268 (1988).

Vander Hooven, "Corncob Granules and Pelleted Carriers—New, Controlled, Safer Methods of Handling Pesticides," In Kaneko/Akesson (eds.), Pesticide Formulations and Application Systems: Third Symposium, ASTM STP 828, American Society for Testing and Materials, Philadelphia, pp. 132–149 (1983).

Weissling et al., "Potential of Starch Encapsulated Semiochemical/Insecticide Formulations for Adult Corn Rootworm (Coleoptera: Chrysomelidae) Control," J. Econ. Entomol. 84: 601–609 (1991).

Wing et al., "Determination of Reaction Variables for the Starch Xanthide Encapsulation of Pesticides," J. Polym. Sci. Polym. Chem. Ed. 21: 121–140 (1983).

Trimnell et al, "Autoencapsulation : A New Method . . . ," J. Contr Release, 7 : 25–31 (1988).

Trimnell et al, "Autoencapsulation . . . Starch," J. Controlled Release 7 : 25–31 (1988).

Trimnell et al, "Entrapment . . . Applications," J. Controlled Release 7 : 263–268 (1988).

McGuire et al., Field Evaluation . . . (Lepidoptera: Pyralidae), J. Economic Entomology 83: 2207–2210 (1990).

McGuire et al., "Evaluation . . . Entomoopoxviruses," J. Econ. Entomol., In Press.

METHODS AND COMPOSITIONS OF ADHERENT STARCH GRANULES FOR ENCAPSULATING PEST CONTROL AGENTS

BACKGROUND OF THE INVENTION

1. Field of the Invention

The present invention pertains generally to methods and compositions related to control of pests (e.g., insects, weeds, plant pathogens), more specifically insects, and more particularly to control of insects on plant foliar surfaces. The invention especially concerns adherent granules made of starch that are carriers for pest control agents, and methods to produce said granules.

2. Description of the Related Art

Myriad approaches have been pursued to control pests. Many of these methods and compositions are directed to control of pests that attack plants, most notably commercially valuable plants. Although much current agricultural research has pest control as its objective, pest destruction of plants and plant products is still a major problem.

Pesticides, biological or chemical agents that kill pests, have been encapsulated in starch which was crosslinked with borate, calcium, or xanthide, thereby producing a matrix that can be processed into granules of desired sizes and densities (Shasha et al., 1984; Trimnell et al., 1982; Wing et al., 1983). However, these methods cannot be used for most living biological pesticides because the reagents and conditions are too harsh for their survival.

Controlled release by means of starch-based encapsulating materials can also be accomplished without the use of chemical crosslinking reactions. In U.S. Pat. No. 2,876,160, Schoch et al. disclose such a method which employs modified, amylose-free starches at concentrations up to 65% solids for embedding water-soluble materials.

In PCT Int. Appl. WO 85/04074, Flashinski et al. disclose two methods of preparing a starch gel matrix containing an insecticide. The insecticide is either coextruded with a dilute, aqueous dispersion of starch, or the starch is first partially cooked in an extruder prior to cold-blending with the insecticide. In either case, the product is recovered and used as an aqueous gel.

In U.S. Pat. No. 4,230,687, Sair et al. disclose the application of shearing stress, vigorous mechanical working, and heat to distribute an active agent into an enveloping matrix of chemically modified starches, gums, and proteins in the presence of a limited quantity of water. Proteins are used for slow-release matrices; modified starches are used for rapid release.

Similarly, in U.S. Pat. No. 3,922,354, Galuzzi et al. disclose the use of high-shear mixing to incorporate active agents into low-water, high-solid matrices prepared from partially gelatinized unmodified starches. Additives such as modified dextrins, mixtures of mono- and diglycerides, toasted cereal solids, and coloring agents are used to control the release of active agents.

In U.S. Pat. No. 3,666,557, Jensen et al. disclose a method of using low-fat starchy materials to microencapsulate individual beadlets of sensitive materials such as vitamins and vegetable oils. Starches are prepared for encapsulation by heating at 88° C. for 30 min followed by passage through a homogenizer to effect disruption of granules without degradation of molecules.

One general approach has been to develop carriers for insect control agents. Controlled-release systems based on entrapment of insect control agents in natural polymer matrices have some advantages. For example, hydrated hydrogel capsules have been used to incorporate insecticidally effective amounts of nematodes (U.S. Pat. No. 4,701,326). Capsules in that patent were designed to prevent desiccation. Other types of carriers have been granules.

Insecticides have been formulated on various granule carriers (Synek, 1983; Vander Hooven, 1983). Clay granules have been used to encapsulate entomopathogens (Raun et al., 1966). These carriers may be classified as baits which the insect must feed upon, or inert particles such as clay or corn cob which carry the active agent to the target site and then depend on environmental factors to release the active agent into the feeding zone. Baits have been used in control efforts against grasshoppers (Shotwell, 1944) and, more recently, against European corn borers (McGuire et al., 1990). Because baits must be ingested, they are much more specific than either liquid sprays, dusts, or inert granule carriers.

Integrated pest management programs against ground-dwelling insects such as the fire ant and certain grasshopper species that require selective pesticide usage are areas of application for these types of baits. However, currently available baits have limited utility for controlling most leaf-feeding pests because the granules are easily dislodged from the feeding zone, thus rendering them ineffective against the target pest. Additionally, theoretical calculations show that at application rates of 1 lb/A, less than 0.01% of the leaf area is covered, assuming particle sizes of approximately 1-mm diameter (Koestler, 1980). To maximize the chances of an insect discovering the granule, volatile attractants may be incorporated into the formulation (e.g., Meinke et al. 1989; Metcalf and Lampmann, 1989; Lance and Sutter 1990).

The granule carriers for insect control agents have generally been suitable only for control of soil-borne pests. They have not been useful for foliar control of insects on plants because they have difficulties sticking to the foliage, or being consequently susceptible to removal by wind, rain, or other disturbing forces. Granule carriers for foliar insect control have neither been efficient nor economic.

Methods for encapsulating entomopathogens within starch matrices have been developed (Dunkle and Shasha, 1988; and U.S. Pat. No. 4,859,377). Recently, a series of papers has examined the potential for using the Dunkle and Shasha (1988) techniques. One class of agents which were encapsulated within these starch matrices were bacteria, most notably *Bacillus thuringiensis* Berliner for control of European corn borers (McGuire et al., 1990). Grasshopper entomopoxvirus for control of rangeland grasshoppers was similarly formulated (McGuire, et al., 1991).

In another application the starch encapsulation process for preparing a formulation was used to control adult *Diabrotica spp*. (e.g., Lance and Sutter, 1990; Weissling and Meinke, 1991). Ingredients in the formulation included an attractant, a feeding stimulant (cucurbitacin), and a small amount of insecticide. Although preliminary results were promising, the formulation would not stay in the feeding zone. The development of new, adherent granules is required to aid in this bait approach. A significant problem is that traditional baits generally do not stick well to plant foliage and soon disappear from the feeding zone of the target insect, requiring constant and costly replenishment.

Pesticides were encapsulated by starch xanthate, but methods of production were undesirable due to flammable and toxic components. Other starch-based systems are reviewed by Trimnell and Shasha (1988). These required large numbers of steps placing severe limitations on their commercial use.

A method was developed by Trimnell and Shasha (1988) to form carrier starch granules using relatively small amounts of water. In the Trimnell and Shasha method, a pesticide was mixed with the pregelatinized starch or ungelatinized starch containing a gelatinizing agent and sufficient water to form granules. The sequence of steps in their method was first to mix a solution of chemical herbicide and an organic solvent, and subsequently to add water. By this method granules were formed that encapsulated the pesticide upon contact with the free water. However, these granules required further processing that limited their usefulness.

In addition to deficiencies in the composition of the starch granules, the methods of producing the granules with living entomopathogens also have serious limitations which become more glaring the more scaled up the production. The basic method (Shasha and Dunkle, U.S. Pat. No. 4,859,377) consists of adding water to modified starch at a proportion of at least 1:1 to produce a gelatinous mass. Unfortunately, when the laboratory procedures were scaled up to achieve mass production of the granules, the high water content caused difficulties. Heat could not be applied as a drying agent because entomopathogens will not survive the heat required to effect drying and, thus, would lose their effectiveness. The persistently high water content made grinding and drying of the gelatinous starch mass to produce granules not feasible for most commercial production. Simply reducing the water content resulted in uneven distributions of moisture in the mass.

In summary, despite numerous methods and compositions proposed for pest control, efficacy of granular pest control agents applied to surfaces, for example, plant foliar surfaces, has not been attained.

SUMMARY OF THE INVENTION

The methods and compositions of the present invention solve a significant number of the problems of delivering biologically active agents to a target site by producing granules which can encapsulate such agents and are capable of adhering to plant foliage despite exposure of the plants to environmental forces which dislodge other types of granules.

In one embodiment of the invention, the adherent granules are formed by (a) providing a mixture of pregelatinized starch, water, a volatile organic solvent, and a biologically active agent and (b) exposing the mixture to conditions sufficient to permit evaporation of the solvent and formation of granules comprising the active agent in starch.

In another embodiment of the invention, a solution comprising water, an inorganic salt and an active agent is added to a dispersion of pregelatinized starch to gel the starch into granules comprising the agent.

The granules produced in accordance with these embodiments, upon application to wet surfaces and being allowed to dry, will adhere to those surfaces even in the presence of additional water. Because this invention also provides new and improved methods for mass production of said granules, cost decreases, and efficiency increases.

DETAILED DESCRIPTION OF THE INVENTION

Figure 1A:
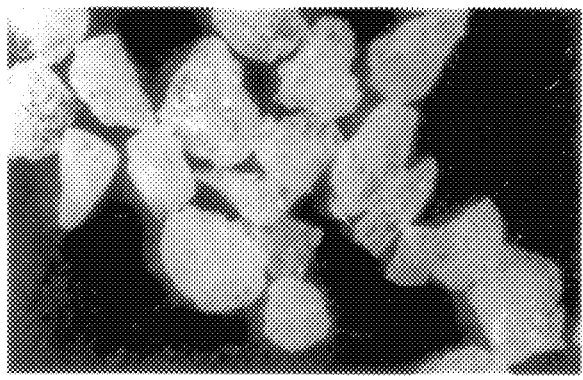
FIGS. 1A–1F are light stereomicrographs of granular products produced from the pregelatinized starch "Miragel".

This invention relates to novel methods of preparing and using starch-based carriers in granular form to deliver insect control agents to plant surfaces, and to the composition and structure of these granules.

Starch is a readily obtainable natural polymer, composed of amylose and amylopectin, is relatively inexpensive and is capable of forming films. Amylose is essentially a linear polymer having a molecular weight in the range of 100,000–500,000, whereas amylopectin is a highly branched polymer having a molecular weight of up to several million. When starch is gelatinized in water and cooled, the amylose retrogrades to a much greater extent than the amylopectin fraction. Retrogradation is a term applied to the phenomenon whereby starch chains in dispersion associate, become insoluble, and precipitate. The rate and extent of retrogradation depends on the properties of the dispersion (pH, temperature, concentration) and on the amount of amylose present in the dispersion. Common cornstarch (pearl) contains about 25% amylose and 75% amylopectin; whereas the waxy corn starches contain only amylopectin. High-amylose starches contain up to 75% amylose.

The staring encapsulating material for use in the invention includes any pregelatinized starch which will form a gel upon rehydration in an aqueous medium, and thereafter be amylase-digestible. Pregelatinized starches are commercially available or are prepared by cooking the starch at elevated temperatures ranging from 70° to 120°, preferably about 80° C. for a time ranging from 5 sec to 30 min, preferably about 10 min, and precipitating the cooked starch. In a preferred embodiment for use with organic solvents, the starch includes modified cornstarch. The starch ingredient may be selected from a group comprising: pregelatinized pearl cornstarch, pregelatinized corn flour, pregelatinized waxy cornstarch, pregelatinized potato amylopectin, and mixtures thereof. A commercial pregelatinized starch useful herein is "Miragel" (Staley Inc., Decatur, Ill.), a fully pregelatinized pearl cornstarch. Other suitable starch sources which are useful upon gelatinization by conventional procedures include: "Flour 961" (Illinois Cereal Mills, Paris, Ill.), a corn flour that passes 60 mesh; "Amylon 5" (National Starch and Chemical Co., NJ), a starch which contains about 50% amylose; and "Staco M" (Staley Co.), a low viscosity, oxidized cornstarch that passes 30 mesh.

This invention relates to several solutions to the problem of granule adherence. A key element of one of the methods for granule production disclosed herein, is the use of water-soluble organic solvents in the granulation process. The results of this is a surprising and unexpected discovery, because water-soluble organic solvents are well known to those of skill in the art not to gelatinize starch. Surprisingly, these solvents were one of the keys to solving the puzzle of how to encapsulate pest control agents in dry granules, and yet have those granules be able to adhere to plant surfaces.

In an illustrative embodiment, pregelatinized cornstarch is blended with an azeotropic mixture consisting of water and an organic solvent. The azeotrope allows the granules to dry faster than if only water is used. Dry granules subsequently were produced by this simple method, yet tests showed that the granules adhere extremely well to plant surfaces in the presence of moisture when applied to the plants.

These granules are capable of acting as carriers for various biologically active agents, particularly pest control agents and other agricultural materials. Pests are defined herein to include insects, weeds, plant pathogens, and any other agents deleterious to organisms of interest, particularly plants. Accordingly, exemplary agents contemplated for encapsulation in accordance with the invention include without limitation insecticides, herbicides, fungicides, nematicides, nematodes, fertilizers, volatile attractants, or other similar components or combinations thereof.

The methods of this invention are suitable for either chemical or living pest control agents. Contemplated for insect control are chemical pesticides such as thiocarbamates, dinitroanilines, and organophosphates, specifically, malathion, carbaryl, alachlor, and diazinon. Embodiments of biological pest control agents comprise bacteria, such as *B. thuringiensis;* viruses, particularly Baculoviridae, such as *Autographa californica* nuclear polyhedrosis virus; nematodes, protozoa such as *Nosema spp;* and fungi such as Beauveria.

Attractants include, but are not limited to, aqueous, nonsoluble, or hydrophobic substances which are capable of attracting insects to the granule or of stimulating ingestions of the granule. Illustrative of attractants are pheromones and p-methoxycinnamaldehyde. Feeding stimulants which are suitable include powdered, dried root of the buffalo gourd. Additives, for example, sunscreens such as charcoal or Congo-red, and vitamins are other optional ingredients which may be encapsulated in accordance with this invention.

There are various proportions of starch, water and solvent which are suitable for the present invention. In a preferred embodiment, the ratio of these three components is about 10:7:3, respectively. In general, the ratio of water to solvent must be high enough to form at least small granules when mixed with starch but also this ratio must be low enough so that a single mass is not formed. A range of 10–50% solvent is preferred. A 30% solution of solvent in water is added in about a 1:1 ratio to the starch in a preferred embodiment. An advantage of the mixing sequence, which is an aspect of this invention, is that evaporation of solvent is minimized, thereby reducing the likelihood of forming gelatinous masses not having the desired characteristics of discrete granules of encapsulated agent.

In another preferred embodiment of the invention, adherent granules are prepared by combining pregelatinized starch with calcium chloride or another suitable inorganic salt dissolved in a small amount of water. Partial or whole substitution of various inorganic salts for the volatile water-soluble organic solvents of the aforementioned embodiment is suitable. Upon mixing gelatinized starch with a water solution containing an inorganic salt such as calcium chloride, ammonium sulfate, sodium sulfate, sodium carbonate, or a combination of sodium sulfate with sodium carbonate, discrete granules are formed which also have adherent properties. Optionally, the salt may be dry-mixed with the starch prior to the addition of water or the salt may be combined with solvent and mixed with gelatinized starch to form similar particles.

The minimum amount of salt required must be enough to avoid the formation of a single gelatinous mass upon initial mixing. The maximum amount of salt is limited by saturation of the water with the salt at room temperature. Optimally, about 50% of saturation is desirable.

Granules prepared in this fashion have adherent properties similar to those prepared with organic solvents as described herein. A possible explanation for the results observed using this method is that when salt is dissolved in the water prior to the addition of starch, the water is not readily accessible to the starch. This competition for the water between the solubilized salt and the starch delays gelling of the starch. Eventually, as the starch absorbs the water, granules will form similarly to the process of granule formation in the solvent-water system.

An illustrative embodiment of a method of use of the granular products of the invention granules comprises choosing at least one active agent, encapsulating an effective amount of that agent in the starch component as disclosed herein, and applying the granules to plant surfaces. The active agent of choice will depend on the target species and the nature of the plants to which the encapsulated material is to be applied. An effective amount is defined herein to mean that amount which includes the desired response in the target organism. For example, a "pesticidally effective amount" is defined to mean those quantities of agent which will result in a significant mortality rate of a test group as compared to an untreated group. The actual amount may vary with the species of pest, stage or larval development, the nature of the substrate, the period of treatment, and other related factors.

In a typical application, the granules are applied to the plant foliage as a free-flowing particulate. When contacted with water preexisting on the foliage surface or subsequently provided, the starch gels promote adherence of the granules to the foliage. Water for filed conditions may be supplied by rainfall, nocturnal condensation, dew, or irrigation. Once adhered to the plants, the granules are resistant to environmental disturbances including wind, rain, and snow.

The data shown herein (Example 3) demonstrate that *B. thuringiensis* insecticidal activity does not change when the granular products are formulated using 2-propanol. The alcohol apparently was not in high enough concentration or did not persist long enough to either kill the spores of denature the parasporal crystals. The methods and compositions for producing adherent granules is very versatile and allows for the incorporation of sunscreens or other additives to protect or enhance bacterial activity.

Some of the advantages of the methods and compositions of the present invention include: (1) avoidance of direct contact of the pest control agent with the foliage, reducing risk of dermal phytotoxicity occurring in treated plants; (2) decreased environmental pollution due to reduced evaporation of the insect control agents and biodegradability of the control composition; (3) more effective control over the release period of the agent; (4) simplicity; and (5) maintenance of the chemical composition of the agent to be delivered to the plants (i.e., the active agents tend not to degrade or volatilize). Another advantage is that lower levels of the active agent may be applied to achieve the same level of control as achieved by commercial formulations containing higher levels of active agent. Safety to handlers, is thereby increased. Yet another advantage of this invention is that insect control agents such as pesticides which are labile under alkaline or acidic conditions may be formulated under neutral conditions using starch-based systems.

The use of the adherent granular bait compositions of the present invention results in a likely decrease in the total amount of pest control agent applied per area because food or sex attractants may be incorporated to bring pests to the bait instead of relying on complete coverage of the area. The possibility of a longer residual effect due to adherence allows for earlier application and extends the "window" of application necessary for the economic control of a pest that may enter an area over an extended period of time. Furthermore, data disclosed herein shows sustained release over time of agents and other ingredients incorporated into the subject granules.

In the embodiment of the present invention which employs addition of organic solvents, the organic solvent-water system facilitates aggregation of starch and the other ingredients of the formulations contemplated herein. The adherence of granules varies with different starch types. While pearl cornstarch contains about 25% amylose, waxy cornstarch contains mostly amylopectin, and "Amylon 5" contains about 50% amylose. Treatment of pregelatinized starch, especially starch composed of both amylose and amylopectin, with a water-2-propanol solution yields significantly improved products over commercial formulations; namely, enhanced adherence to substrates (Examples 5–8).

Figure 1D:
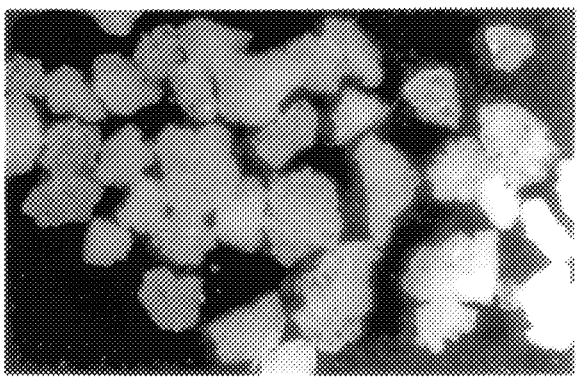
Figure 1B:
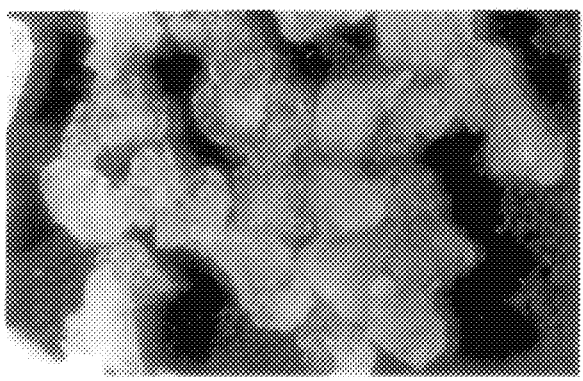
Figure 1E:
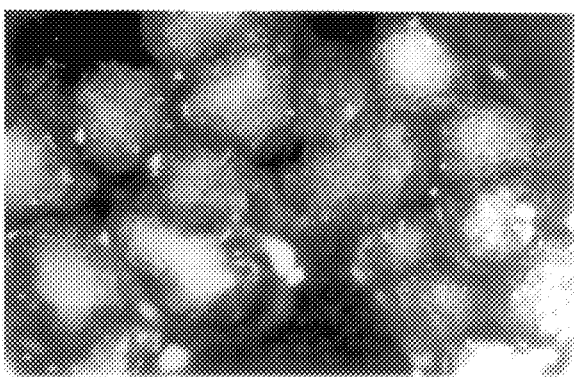
Figure 1C:
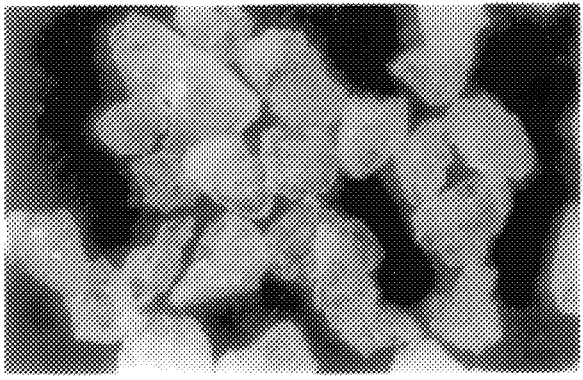
Figure 1F:
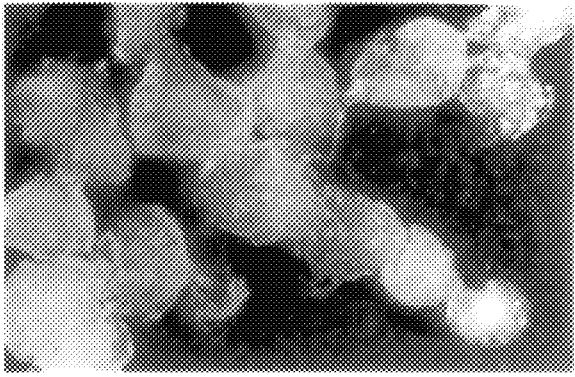

Dry and wet samples of granules made with "Miragel" were observed under a light stereomicroscope and through SEM to elucidate the adherence phenomenon. "Miragel", which is commercially available, is made from pearl cornstarch that has been fully pregelatinized. FIG. 1 presents light stereomicrographs of granules made of "Miragel" prepared with water only FIGS. 1A–1C or with a 30% 2-propanol solution FIGS. 1D–1F. FIGS. 1A and 1D are dry granules before wetting; FIGS. 1B and 1E are wetted granules; FIGS. 1C and 1F are granules after drying. Granules made with 2-propanol were not fully gelled initially, but after wetting adhered both to each other and to the glass surface.

The methods and compositions of the present invention are significant improvements over previous art. Starch granules made by previous methods, e.g., those reported by Dunkle and Shasha (1988) did not adhere to glass slides. By using water in combination with water miscible organic solvents, the product adhered to surfaces. In exemplary embodiments, in which certain organic solvents were added to the formulation prior to gelatinization, granules became adherent and resisted wash-off. Table I shows the effect of organic solvent type on adherence of "Miragel" granules.

Examination of granules by use of a stereomicroscope before wetting the granules, showed that granules made with 2-propanol were more opaque than granules made without 2-propanol (FIG. 1). When wet, both types of granules became transparent but after drying, a difference was observed. Granules made with 2-propanol adhered to each other as well as to the glass slide, whereas granules made only with water remained distinct and appeared similar to granules that had not been wetted.

Figure 2A:
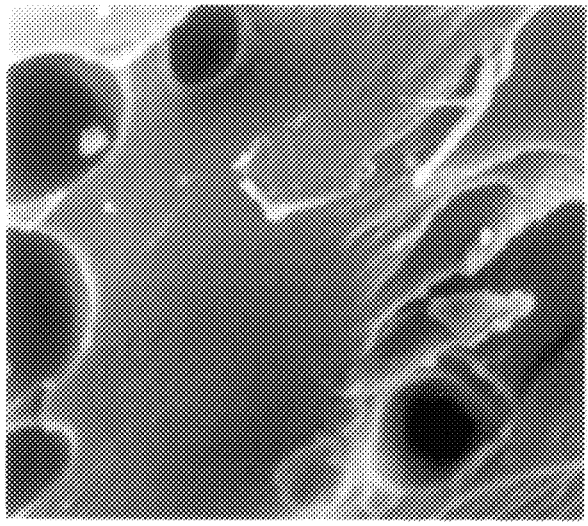
FIGS. 2A–2D are scanning electron micrographs of dry starch granules.
Figure 2B:
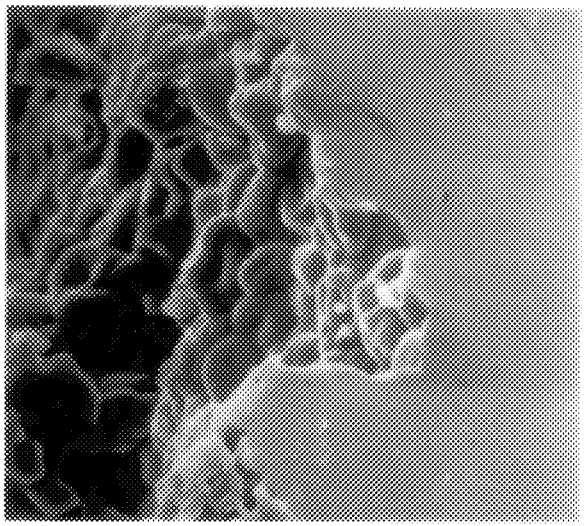
Figure 2C:
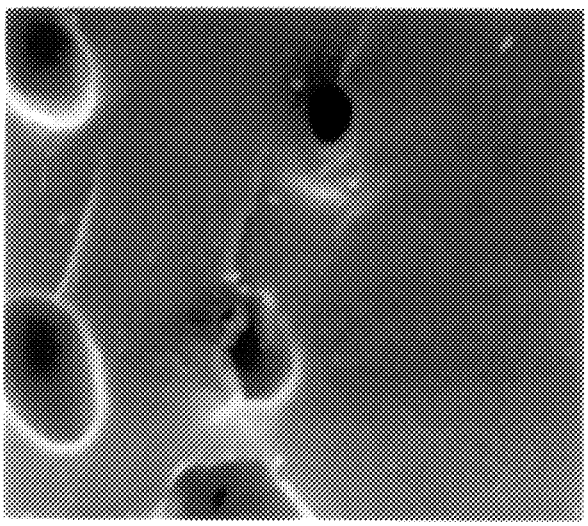
Figure 2D:
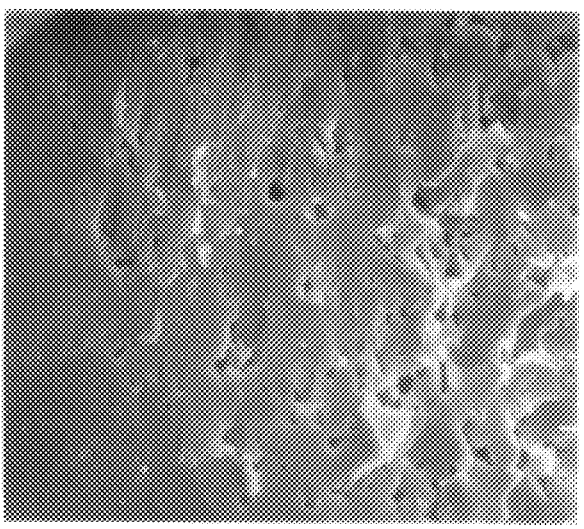

Examination of granules with a scanning electron microscope before wetting (FIG. 2), revealed obvious differences between granules made with water only (FIGS. 2A and 2C) and granules made with 2-propanol (FIGS. 2B and 2D). Externally (FIGS. 2A and 2B), ungelled starch grains were observed on granules made with 2-propanol, whereas no such grains were observed on granules made with water alone. Additionally, smooth surfaces were observed indicating that some of the grains did gel. Internally, many small pores were observed in granules made with 2-propanol, but no such pores were observed in granules made with water only (photomicrographs taken at 700×).

Figure 3A:
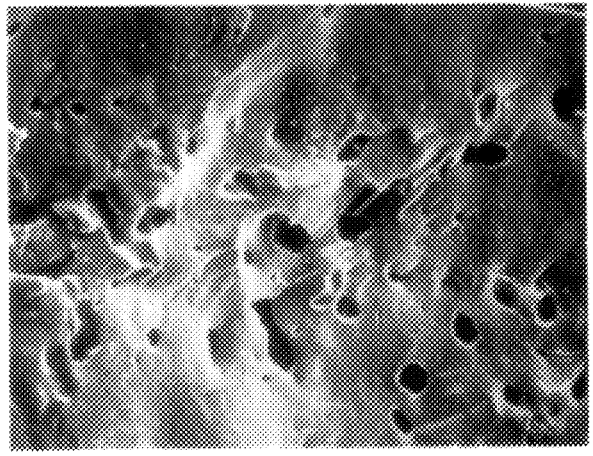
FIGS. 3A–3D are scanning electron micrographs of starch granules after wetting and subsequent drying.
Figure 3B:
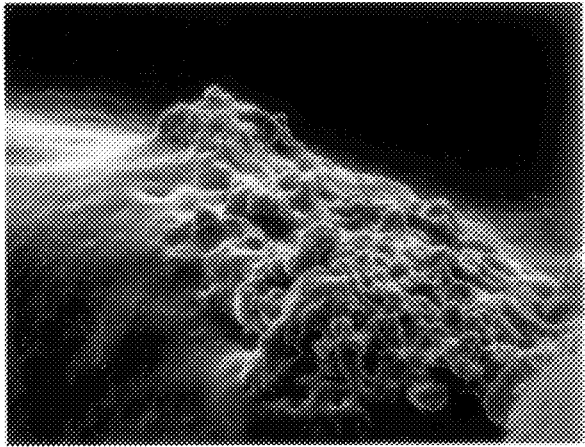
Figure 3C:
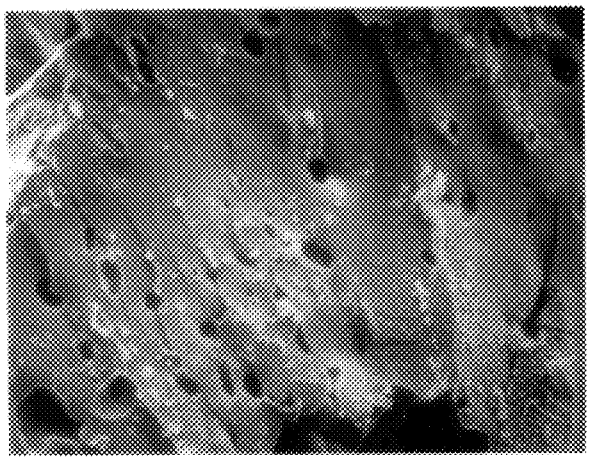
Figure 3D:
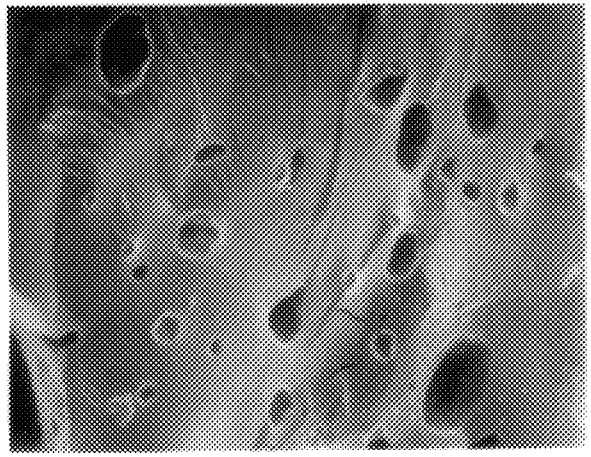

After wetting and subsequent drying, scanning electron micrographs (FIG. 3) show that differences between the two types of granules were not as apparent. The surface of granules made with 2-propanol (FIG. 3B) became much smoother as the ungelled starch grains gelled upon contact with water. Internally (FIG. 3D) the small pores disappeared, and the granules resembled granules made with water only (FIG. 3C). The granules made with water only (FIGS. 3A and 3C) did not change in appearance after wetting. (Photomicrographs taken at 250×).

In still another variation of the invention, granular starch-encapsulated agents prepared by the aforementioned processes or by other processes as known in the art can be coated with an additional layer of pregelatinized starch. One suitable starch for this purpose is the aforementioned "Miragel". Another suitable pregelatinized starch is substantially free of amylose and is commercially sold under the trade name "Mirasperse" (A. E. Staley Co. Decatur, Ill.). The coating is readily accomplished by first wetting the outside of the granule with water, and then contacting the wetted granule with the pregelatinized starch. The advantage of such a coating is that it can serve to tailor the release rate of the active agent. Also, for those types of granules which are not inherently adherent as are those produced in accordance with the aforementioned embodiments of the invention, the added coating tends to make such granules adherent when subsequently contacted with water.

An incidental aspect of this invention relates to an assay to screen various formulations made in accordance with the disclosed processes, particularly in regard to ranking the formulations by relative stickiness of the resulting granules. This screening assay is useful commercially because it minimizes the cost of testing various formulations by substituting laboratory tests on glass slides for field tests on actual plants. Not only is cost reduced, and space and time saved, but there is absence of risk to the plants if the formulations do not work, whereas field tests of ineffective compositions leave the plants vulnerable to pest attack.

An embodiment of the laboratory adherence assay is to treat pre-weighed, pre-cleaned glass microscope slides, and to sprinkle the granules to be tested on the moistened slide. The slides containing the granules on its surface are subjected to a stream of distilled water. An even flow of water is achieved by movement of the slide under the stream.

MATERIALS AND METHODS

The following materials and methods were employed in the ensuing examples.

A. Formulation Ingredients (Starch and Solvent)

"Miragel" starch is a pregelatinized corn product marketed for use in the food industry. "Flour 961" (Illinois Cereal Mills, Paris, Ill.), pearl cornstarch (CPC International, Englewood Cliffs, N.J.), waxy cornstarch (American Maize Products, Hammond, Ind.), potato amylopectin and "Amylon 5" (National Starch and Chemical Co., NJ), and "Staco M" (Staley, Co.) starch were all gelatinized using standard procedures. Briefly, 100 g starch were added to 1 liter water and cooked for 10 min at 80° C. to cause gelatinization. After cooling to 50° C. but before retrogradation occurred, starch was isolated by precipitation with 3 liters of 95% ethanol in a blender. The dispersion was filtered and washed with absolute ethanol to remove trace water, and then dried. Methanol, ethanol, 2-propanol, acetone, n-butanol, and 1,4-dioxane were all reagent grade.

B. Glass Slide Assays

To initially screen a large number of formulations without using plants, a simple assay was developed to determine the relative stickiness of the granules. Pre-weighted, pre-cleaned glass microscope slides were wetted by spraying distilled water on one surface. Twenty milligrams granules were carefully sprinkled on the wet surface and allowed to dry. The slides were then placed approximately 2 cm under a stream of distilled water from a burette. Forty ml of water were allowed to flow from the burette at the rate of 20 ml/min over the slide and the slide was moved back and forth constantly to maintain a flow of water evenly over the glass surface. Slides were allowed to air dry and the procedure was repeated for a total of four wash/dry cycles. Slides were then weighted to determine granule loss. Five slides were prepared for each formulation.

The glass slide assay procedure was used to test the effect of the solvents used in the formulation process. Results were analyzed by analysis of variance (ANOVA) and means were compared using the least significant difference test (Lund, 1988).

The glass slide assay procedure was also used to examine the effect of 2-propanol solution on adherence of granules made with the various starches. As controls, granules were made with water only and tested in parallel with granules made with 2-propanol. Results were analyzed in a 2×2 factorial design with starch type (6 degrees of freedom) and 2-propanol presence or absence (1 degree of freedom) as main effects.

Plant Leaf Assays

Although the glass slide assay provided preliminary information concerning adherence properties of the granules, it was necessary to develop an assay utilizing plant tissue to more accurately demonstrate these properties. Cotton was selected as the test plant because it grew easily in the greenhouse and provided a flat leaf conducive to application and removal of granules. An area of 33 sq cm was marked on the leaf by tracing around the mouth of a 150-ml beaker with a permanent marker. This area was wetted with distilled water and then 30 mg granules were carefully sprinkled onto the area.

After drying, 10 leaves were removed and the granules were scraped off, dried, and weighted. To determine the effect of moisture on adherence, distilled water was applied to each leaf area after granule application. A garden variety pump sprayer fitted with a pressure gauge was used to apply approximately 5 ml water at 15 psi to each remaining leaf three times over a 7-day period. The nozzle and distance from the leaf were adjusted so that the cone spray pattern just covered the marked area. Seven days after application, 10 additional leaves were excised, and the granules were treated as above.

The following examples are intended only to further illustrate the invention and are not intended to limit the scope of the invention which is defined by the claims.

EXAMPLE 1

The Effect of Solvent on Adherence

To prepare granules for testing the effect of solvent type on adherence to substrates, 50 g "Miragel" was mixed with 50 ml of a 30% solution of the test solvent in water. Solvents tested included 2-propanol, methanol, ethanol, n-butanol, acetone, and dioxane. After allowing for time sufficient for the gelled mass to retrograde and become less sticky, the mass was broken apart in a blender or crumbled to create particles that passed 20 mesh but not 40 mesh. This corresponds in general to particle sizes of 850 µm to 425 µm in diameter after drying. Some formulations crumbled easily without the aid of a blender.

Granules prepared as described above were subjected to the glass slide assay. As shown in Table I, granules prepared using 2-propanol resisted wash-off from glass slides the most compared to other solvents. Methanol had much less of an adherence effect (83% loss). The other solvents tested were intermediate in effect between 2-propanol and methanol. Generally, a 30% solvent solution in water is preferred, being added subsequently in a 1:1 ratio to starch.

Granules prepared as described above were also subjected to the plant leaf assay. As shown in Table I, solvent type had a significant effect on adherence to cotton leaves both initially (analysis of variance, F=12.87, df=6,63, P<0.001), and after 7 days (analysis of variance, F=10.49, df=12.87, df=6,63, P<0.001). Granules made with water only did not adhere well, whereas granules made with ethanol, 2-butanol, and 2-propanol adhered the most after 7 days.

TABLE I

Effect of Organic Solvent Type on Adherence of "Miragel" Granules

| Solvent[a] | Mean % loss of granules on slides[b] | Average mg granules on cotton leaves days after appl. 0 | 7 |
|---|---|---|---|
| water | 100.0 A | 15.5 A | 2.4 A |
| 2-propanol | 2.5 F | 27.6 CD | 16.7 D |
| methanol | 83.0 B | 23.6 B | 7.1 B |
| ethanol | 13.5 DE | 28.2 D | 14.1 CD |
| n-butyl alc. | 10.5 E | 28.8 D | 15.6 CD |
| acetone | 39.5 C | 25.9 BCD | 7.2 B |
| 1,4-dioxane | 18.5 D | 24.2 BC | 11.9 C |

[a]Granules were prepared by mixing 50 g "Miragel" with 35 ml water and 15 ml solvent.

[b]Means followed by same letter within a column are not significantly different (least significant difference P < 0.05).

EXAMPLE 2

The Effect of Starch on Adherence

To prepare granules for testing of the effect of starch type on adherence to substrates, 50 ml of a 30% 2-propanol solution were added to 50 g of the gelatinized test starch. The gelatinized mass was treated as above. Test gelatinized starches includes those listed in "Formulation Ingredients", supra.

Although 2-propanol had a significant effect on adherence to glass slides over all starches tested (analysis of variance, F=1268.25, df=1,56, P<0.001), not all starches heaved the same with respect to the addition of 2-propanol. There was a significant effect due to starch type (F=142.88, df=6,56, P<0.001). Furthermore, a significant interactive effect (F=102.52, df=6,56, P<0.001) indicated that not all starches behaved the same with respect to addition of 2-propanol. In an illustrative embodiment granules made with "Miragel" and gelatinized pearl starch exhibited the greatest level of adherence when made with 2-propanol. Granules made from gelatinized "Amylon 5" or gelatinized "Staco M" showed to adherent properties on glass when mixed with 2-propanol. Other starch products (gelatinized waxy and gelatinized potato amylopectin) demonstrated intermediate properties in relation to adherence.

Starch type also yielded a significant effect with respect to adherence to cotton leaves, when granules made with and without 2-propanol were combined, (analysis of variance, F=30.89, df=6,126, P<0.001). Gelatinized "Amylon 5" did not adhere well while "Miragel", gelatinized waxy, and gelatinized pearl starch all adhered equally well. As with glass slides, a significant interaction occurred (analysis of variance, F=15.26, df=4,90, P<0.001) because 2-propanol had a large influence over adherence of all starches except gelatinized "Amylon 5". The 2-propanol had a significant effect on adherence of various starch granules to cotton leaves after 7 days (analysis of variance, F=342.51, df=1, 126, P<0.001) (Table II).

TABLE II

Effect of Starch Type and Presence of 2-Propanol on Adherence of Granules

| Formulation No.[a] | Starch Type | % Loss of granules from slides | Average mg granules on cotton leaves days after appl. 0 | 7 |
|---|---|---|---|---|
| 1A | Gelatinized Amylon 5 | 100 | 19.5 | 0.0 |
| 1B |  | 100 | 22.1 | 0.1 |
| 2A | Gelatinized Flour 961 | 100 | 18.13 | 1.29 |
| 2B |  | 10 | 24.15 | 14.54 |
| 3A | Gelatinized Waxy | 75 | 27.3 | 4.9 |
| 3B |  | 40 | 29.0 | 20.6 |
| 4A | Gelatinized Pearl | 100 | 25.0 | 7.7 |
| 4B |  | 9 | 27.7 | 18.5 |
| 5A | Gelatinized Staco M | 100 | 27.3 | 1.7 |
| 5B |  | 100 | 27.0 | 16.5 |
| 6A | Gelatinized Potato | 100 | 21.04 | 0.76 |
| 6B | Amylopectin | 50 | 25.48 | 21.41 |
| 7A | Miragel | 100 | 27.0 | 9.5 |
| 7B |  | 2.5 | 25.9 | 15.3 |

[a]25 g starch was mixed with (A) 50 ml water or (B) 35 ml water and 15 ml 2-propanol.

EXAMPLE 3

Bioassay with *B. thurigiensis*

To test the effect of the 2-propanol-containing formulation on survival of insecticidal activity of *B. thuringiensis*, granules were prepared as described above with a 30% solution of 2-propanol except *B. thuringiensis* technical powder (supplied by Abbott Laboratories) was added at the rate of 1600 International units per mg of dry ingredients. As controls, granules were similarly prepared with water alone and both formulations were prepared without *B. thuringiensis*. These four granule types were then assayed for insecticidal activity against European corn borer (*Ostrinia nubilalis* Hubner [Lepidoptera: Pyralidae]) neonates. Assays were initiated by incubating 100 mg granules in 2 ml distilled water containing 2 mg α-amylase at 37° C. for 1 hour. The suspension was diluted to 8 ml with water and then homogenized for 10 sec in a "Virtishear" tissue homogenizer (Virtis) at full power. Two milliliters of green food coloring were then added. Sixty neonate corn borers were allowed to feed on droplets of the suspension (Hughes and Wood, 1981) and were then transferred individually to plastic cups containing artificial diet. Percent mortality was obtained 2 days later. This experiment was conducted twice, each with freshly prepared granules.

Granules made with *B. thuringiensis* and 2-propanol showed little or no reduction in activity as measured by percent mortality of *O. nubilalis* (52%, 42% in two tests) when compared to granules made in the same manner but without 2-propanol (Table III).

TABLE III

Effect of Encapsulating B.T. in 2-Propanol-Containing Starch Granules on Percent Mortality of *Ostrinia nubilalis*

| Formulation ingredients | IU/mg | Percent mortality* Test 1 | Test 2 |
|---|---|---|---|
| "Miragel" water | 1600 | 48 | 48 |
| "Miragel" water 2-Propanol | 1600 | 52 | 42 |
| "Miragel" water | 0 | 0 | 0 |
| "Miragel" water 2-propanol | 0 | 1.7 | 0 |

*Based on 60 insects/formulation.

EXAMPLE 4

Field Trapping Test

Starch granular formulations were tested to determine how well they attracted the Western corn rootworm, *Diabrotica virgifera virgifera* LeConte. All granules were made with pregelatinized pearl cornstarch, water, 2-propanol, carbaryl (an insecticide), and buffalo gourd root powder, (*Curcurbita foetedissima* H.B.K., a feeding stimulant); p-methoxycinnamaldehyde (PMCn, Schweizerhall, Inc., South Plainfield, N.J.) was used in some formulations as an attractant. Granules were prepared as described in Example 2 using pregelatinized cornstarch, and a 30% solution of 2-propanol. Before gelling, carbaryl (2% AI/dry wt) and the dried, powdered, root of buffalo gourd (5% wt/wt) were added. To determine if a volatile attractant could also be encapsulated and yet be released over a period of time, PMCn, shown by Lampman and Metcalf (1988) to be an attractant for *D. V. virgifera*, was added to the formulation in one of two ways. The attractant was added to the dry ingredients prior to gelling, or granules previously made were soaked in a solvent containing the attractant.

To determine the effect of attractant concentration on granule attractancy, three different concentrations were used approximating 0.1, 1.0, and 10.0% of dry wt. Actual concentrations were determined by soaking the granules in 50% ethanol and measuring absorption at 320 nm in a Beckman DU-50 spectrophotometer. Following formulation, 100 mg granules were placed in vial traps (Shaw et al., 1984) with solid bottoms (Lance, 1988) and placed at ear height in field corn. This experiment was set up in a randomized complete block design with five blocks. A block consisted of a row of corn with vials spaced approximately 10 meters apart.

Blocks were separated by 10 rows. Traps were sampled 3, 6, 9, and 12 days after placement in the field. Additionally, enough traps were initially established so that half of the vials could receive fresh granules after 6 days. Therefore a total of 14 traps were in each block; three with encapsulated PMCn and not changed after 6 days, three with attractant soaked into the granule and not changed after 6 days, and the same six types of granules but changed after 6 days. Two treatments of control granule without attractant were also placed in the field; one treatment was changed after 6 days, the other was not.

There were 14 treatments replicated five times each. Analysis of variance was conducted in a 4×14 factorial design with day and treatment as main effects. Contrasts were then used to determine daily relative effects of changing the granules, the method of attractant addition, and the concentration of attractant. Mean numbers of beetles caught for each 3-day period (Table IV) were subjected to the statistical contrasts presented in Table V. Results of these analysis are presented in Table VI.

Results for each day showed there were fewer beetles trapped in vials with granules containing no attractant than in vials baited with attractant. These results suggest a sustained release of PMCn over the 12-day period (Contrast 1). Except for the first 3 day period, there was no effect due to the position of attractant (i.e., soaked vs. encapsulated) or whether or not granules were changed (Contrasts 2, 3, 6, 7, 8, 9, 10, 11). There was a significant linear relationship with respect to concentration of attractant indicating a dose effect (Contrast 4, 5, 12, 13). There was a significant effect due to the day of capture (F=92.5, df=3,195, P<0.001) because more beetles were caught during the later sampling periods (Table VI). This is likely to represent an increase in the overall population because rootworm emergence continued through the month of August.

TABLE IV

Starch Granular Formulations Tested for Attractancy to D. v. virgifera

| Trap# | % PMCn conc.[a] | PMCn pos[b] | Granules[c] changed after 6d? | Mean beetles/trap days | | | |
|---|---|---|---|---|---|---|---|
| | | | | 3 | 6 | 9 | 12 |
| 1 | 0 | ... | No | 3.6 | 13.2 | 21.8 | 69.8 |
| 2 | 0.095 | enc | No | 0.6 | 30.6 | 26.6 | 71.2 |
| 3 | 0.74 | enc | No | 26.6 | 32.8 | 31.4 | 62.6 |
| 4 | 6.85 | enc | No | 45.6 | 34.0 | 66.4 | 101.2 |
| 5 | 0.095 | Soaked | No | 31.8 | 22.4 | 28.2 | 71.0 |
| 6 | 0.82 | Soaked | No | 48.6 | 50.8 | 55.0 | 77.0 |
| 7 | 8.6 | Soaked | No | 42.0 | 48.6 | 68.8 | 100.4 |
| 8 | 0 | ... | Yes | 7.4 | 16.8 | 21.8 | 64.2 |
| 9 | 0.095 | enc | Yes | 11.4 | 21.2 | 34.0 | 91.4 |
| 10 | 0.74 | enc | Yes | 25.8 | 24.2 | 49.4 | 89.0 |
| 11 | 6.85 | enc | Yes | 41.4 | 35.0 | 56.4 | 87.6 |
| 12 | 0.095 | enc | Yes | 26.0 | 24.8 | 30.6 | 58.8 |
| 13 | 0.82 | Soaked | Yes | 41.4 | 22.2 | 49.4 | 67.6 |
| 14 | 8.6 | Soaked | Yes | 57.6 | 42.6 | 65.8 | 107.8 |
| Total beetles captured | | | | 2099 | 2096 | 3028 | 5589 |

[a]p-Methoxycinnamaldehyde was assayed by soaking 10 mg granules for 1 hour in 100 ml 50% ethanol and then reading absorbance at 320 nm. Readings were compared to standard curve.
[b]p-Methoxycinnamaldehyde was added to the formulations prior to gelling (enc) or granules previously prepared were soaked in solvent containing PMCn.
[c]All granules were made with pregelatinized pearl starch, water, 2-propanol, carbaryl, and buffalo gourd root powder.

TABLE V

Contrasts Used to Determine Differences Among Treatment Combinations (df = 1, 52) for Each Day

| Contrast # | Means compared |
|---|---|
| 1 | Controls vs all others |
| 2 | Enc vs soaked, granules not changed |
| 3 | Enc vs soaked, granules changed |
| 4 | Linear contrast concentration, enc |
| 5 | Linear contrast concentration, soaked |
| 6 | Granules changed vs not changed, concentration/0.1% |
| 7 | Granules changed vs not changed, concentration/1.0% |
| 8 | Granules changed vs not changed, concentration/10.0% |
| 9 | Enc vs soaked, concentration/0.1% |
| 10 | Enc vs soaked, concentration/1.0% |
| 11 | Enc vs soaked, concentration/10.0% |
| 12 | Linear contrast concentration, granules not changed |
| 13 | Linear contrast concentration, granules changed |

TABLE VI

Summary of Results from Contrasts in Table V for Each Day of Trap Counts

| Con-trast | Day | | | | | | | |
|---|---|---|---|---|---|---|---|---|
| | 3 | | 6 | | 9 | | 12 | |
| | F[a] | Pr > F | F | Pr > F | F | Pr > F | F | Pr > F |
| 1 | 35.75 | 0.00 | 13.6 | 0.00 | 34.49 | 0.00 | 4.24 | 0.04 |
| 2 | 6.68 | 0.01 | 2.51 | 0.12 | 4.08 | 0.05 | 0.32 | 0.57 |
| 3 | 9.17 | 0.00 | 0.36 | 0.55 | 0.19 | 0.66 | 2.06 | 0.16 |
| 4 | 42.66 | 0.00 | 9.43 | 0.00 | 53.34 | 0.00 | 6.35 | 0.01 |

TABLE VI-continued

Summary of Results from Contrasts in Table V for Each Day of Trap Counts

| | Day | | | | | | | |
|---|---|---|---|---|---|---|---|---|
| | 3 | | 6 | | 9 | | 12 | |
| Contrast | F[a] | Pr > F | F | Pr > F | F | Pr > F | F | Pr > F |
| 5 | 56.74 | 0.00 | 27.69 | 0.00 | 81.47 | 0.00 | 15.21 | 0.00 |
| 6 | 0.16 | 0.69 | 0.31 | 0.58 | 0.77 | 0.38 | 0.17 | 0.68 |
| 7 | 0.41 | 0.52 | 8.74 | 0.00 | 1.23 | 0.27 | 0.78 | 0.38 |
| 8 | 0.83 | 0.37 | 0.16 | 0.69 | 1.36 | 0.25 | 0.10 | 0.75 |
| 9 | 8.19 | 0.00 | 0.13 | 0.72 | 0.03 | 0.87 | 2.90 | 0.09 |
| 10 | 9.03 | 0.00 | 1.62 | 0.21 | 4.47 | 0.04 | 0.13 | 0.72 |
| 11 | 1.01 | 0.32 | 3.11 | 0.08 | 1.12 | 0.29 | 1.02 | 0.32 |
| 12 | 33.08 | 0.00 | 17.28 | 0.00 | 51.97 | 0.00 | 6.26 | 0.02 |
| 13 | 35.18 | 0.00 | 7.63 | 0.00 | 40.35 | 0.00 | 8.01 | 0.01 |

[a]df = 1,52.

EXAMPLE 5

Inorganic Salt Methods of Preparing Adherent Granules

A. Granules were prepared by first dissolving an inorganic salt in water and combining a portion of this with 30 g "Miragel". As mixing progressed, discrete granules formed. These granules were tested for adherence to glass microscope slides as described, supra. The results of testing granules prepared in this fashion for adherence were as follows:

| Salt type | Salt (g) | Water (ml) | Mixture (ml) | % Loss from slide |
|---|---|---|---|---|
| $CaCl_2$ | 90 | 60 | 8 | 12 |
| KI | 20 | 20 | 12 | 21 |
| $(NH_4)_2SO_4$ | 20 | 40 | 12 | 48 |
| $Na_2SO_4$ | 18 | 40 | 10 | 21 |
| $Na_2CO_3$ | 20 | 50 | 14 | 19 |

B. Granules were prepared by mixing two salts together and adding the mixture to 30 g "Miragel". Only 5% of granules were lost using this method of preparation.

| Salt 1 | Salt 2 | Water (ml) | Mixture (ml) | % Loss from slide |
|---|---|---|---|---|
| $Na_2SO_4$ (10G) | $Na_2CO_3$ (10 g) | 40 | 10 | 5 |

EXAMPLE 6

Combined Use of Organic Solvents and Inorganic Salts in the Preparation of Adherent Granules Granules were prepared by first dissolving an inorganic salt in water, adding organic solvent and then taking some of this mixture and combing with 30 g "Miragel".

| Salt type (g) | Solvent (ml) | Water (ml) | Mixture (ml) | % Loss from slide |
|---|---|---|---|---|
| $FeCl_3$ (10) | Acetone (5) | 15 | 12 | 12 |
| $(NH_4)_2SO_4$ (10) | IPCH (10) | 40 | 14 | 6 |

EXAMPLE 7

Use of Six Granule Formulations with B.T. as an Insecticide: Organic Solvent and Inorganic Salt Methods of Granule Preparation Six different formulations of starch granules were prepared with the entomopathogen *Bacillus thuringiensis* (B.T.). A control was used as a base. These granules were then hydrolyzed with amylase enzyme and fed to neonate *Ostrinia nubilalis* as described in Example 3.

Formulation
1. 43 g "Miragel" was mixed with 35 ml of a solution of 30% 2-propanol. 1 g of B.T. technical powder (from Abbott Laboratories 68,900 IU/mg) was then coated onto the outside of the granules.
2. Same as #1 except 43 ml of 30% 2-propanol was used.
3. Same as #2 except the B.T. was mixed with the "Miragel" before the 2-propanol solution was added. This resulted in the B.T. being evenly dispersed throughout the granule.
4. 90 g $CaCl_2.2H_2O$ was dissolved in 0 ml water. 4 ml of this solution was mixed well with 30 g "Miragel". An additional 4 ml of the $CaCl_2$ solution was then mixed to form granules. 975 mg B.T. was then coated onto the granules.
5. Same as #4 except B.T. was added to the "Miragel" before the addition of the $CaCl_2$ solution.
6. "Miragel" was mixed with B.T. (1600 IU/mg) and then added in equal parts with water. Several hours later, the mass was ground in a "Waring" blender.

The results in terms of percent mortality are shown below:

| Formulation | % Mortality* |
|---|---|
| #1 | 47 |
| #2 | 50 |
| #3 | 55 |
| #4 | 52 |
| #5 | 63 |
| #6 | 42 |
| Control | 0 |

*Based on 60 insects/formulation.

EXAMPLE 8

Adherence to Cotton Leaves of Various Granule Types: Solvent and Inorganic Salt Methods of Granule Preparation Several granule types were prepared and tested for adherence to cotton leaves as described in Examples 1 and 2. The formulations included the following:

Formulation
1. 10 g $(NH_4)_2SO_4$ was dissolved in 40 ml water. 10 ml 2-propanol was then added. 14 ml of this mixture was then added to 30 g "Miragel" and mixed to form granules.

2. 10 g Na$_2$SO$_4$ and 10 g Na$_2$SO$_3$ were dissolved in 40 ml water. 10 ml of this mixture was added to 30 g "Miragel" and mixed with a mortar and pestle to form granules.
3. 20 g KI was dissolved in 20 ml water. 10 ml of this mixture was added to 30 g "Miragel" to form granules.
4. 10 g FeCl$_3$ was dissolved in a mixture of 15 ml water and 5 ml acetone. 12 ml of this solution was added to 30 g "Miragel" to form granules.
5. 20 g (NH$_4$)$_2$SO$_4$ was dissolved in 35 ml water. 10 ml of this solution was added to 30 g "Miragel" to form granules.
6. 15 g (NH$_4$)$_2$SO$_4$ was ground to a fine mesh and added to 15 g "Miragel" in a mortar and pestle. 4 ml water was added dropwise while mixing in the mortar to form granules.
7. 30 g "Miragel" was added to 50 ml of 30% 2-propanol and mixed to form granules.
8. 20 g Na$_2$SO$_4$ (anhydrous) was dissolved in 40 ml water. 10 ml of this solution was added to 30 g "Miragel" and mixed to form granules.
9. 20 g Na$_2$CO$_3$ was dissolved in 50 ml water. 14 ml of this solution was mixed with 30 g "Miragel" with a mortar and pestle to form granules.

The results of adherence of the granules to leaves are shown below:

| Formulation | Days after application* | |
|---|---|---|
| | 1 day | 7 days |
| #1 | 28.97 | 14.85 |
| #2 | 25.94 | 18.28 |
| #3 | 24.90 | 17.43 |
| #4 | 20.99 | 12.07 |
| #5 | 22.83 | 8.69 |
| #6 | 11.78 | 0.62 |
| #7 | 25.59 | 15.50 |
| #8 | 21.50 | 12.84 |
| #9 | 22.43 | 14.78 |

*Granules remaining (mg).

It is understood that the foregoing detailed description is given merely by way of illustration and that modification and variations may be made therein without departing from the spirit and scope of the invention.

REFERENCES

The references listed below are incorporated herein by reference to the extent that the supplement, explain, provide a background for, or teach methodology, techniques, and/or compositions employed herein.

1. Dunkle, R. L., Shasha, B. S. (1988). Starch-encapsulated *Bacillus thuringiensis:* A potential new method for increasing environmental stability of entomopathogens. Environ. Entomol. 17:120–126.
2. Hughes, P. R., Wood, H. A. (1981). A synchronous peroral technique for the bioassay of insect viruses. J. Invertebr. Pathol. 37:154–159.
3. Koestler, R. C. (1980). Microencapsulation by interfacial polymerization techniques—agricultural applications, pp. 117–132. In A. F. Kydonieus [ed.] Controlled release technologies: methods, theory, and applications. CRC Press, Boca Raton.
4. Lampman, R. L., Metcalf, R. L. (1988). The comparative response of *Diabrotica species* (Coleoptera: Chrysomelidae) to volatile attractants. Environ. Entomol. 17:644–648.
5. Lance, D. R. (1988), Responses of northern and western corn rootworms to semiochemical attractants in corn fields. J. Chem. Ecol. 14:1177–1185.
6. Lance, D. R., Sutter, G. R. (1990). Field-cage and laboratory evaluations of semiochemical-based baits for managing western corn rootworm beetles (Coleoptera Chrysomelidae). J. Econ. Entomol. 83:1085–1090.
7. Lund, R. L. (1988). MSUSTAT Statistical Analysis Package, vers 4.1. Research and Development Institute. Bozeman M T.
8. McGuire, M. R., Shasha, B. S., Lewis, L. C., Bartelt, R. J., Kinney, K. (1990). Field evaluation of granular starch formulations of *Bacillus thuringiensis* against *Ostrinia nubilalis* (Lepidoptera: Pyralidae). J. Econ. Entomol. 83:2207–2210.
9. McGuire, M. R., Streett, D. A., Shasha, B. S. In Press. Evaluation of starch-encapsulation for formulation of grasshopper (Orthoptera: Acrididae) entomopoxviruses. J. Econ. Entomol.
10. Meinke, L. J., Z. B. Mayo, and T. J. Weissling (1989). Pheromone delivery system: western corn rootworm (Coleoptera: Chrysomelidae) pheromone encapsulation in a starch borate matrix. J. Econ. Entomol. 82:1830–1835.
11. Metcalf, R. L. and Lampman, R. L. 1989. Cinnamyl alcohol and analogs as attractants for corn rootworms. (Coleoptera: Chrysomelidae). J. Econ. Entomol. 82:1830–1625.
12. Raun, et al. (1966). Encapsulation as a technique for formulating microbial and chemical insecticides. J. Econ,. Entomol. 59:620–622.
13. Shasha, et al. (1984). Starch-borate pesticides for slow release. J. Apply. Polym. Sci. 29:67–73.
14. Shasha, B. S. and M. R. McGuire (1991). Slow release formulations of pesticides. In D. G. Chasin and L. E. Bode, (eds.), Pesticide formulations and application systems. American Society for Testing and Materials, Philadelphia.
15. Shaw, J. T., W. G. Ruesink, S. P. Briggs, and W. H. Luckmann (1984). Monitoring populations of corn rootworm beetles (Coleoptera: Chrysomelidae) with a trap baited with cucurbitacins. J. Econ. Entomol. 77:1495–1499.
16. Shotwell, R. L. (1944). Evaluation of baits and bait ingredients used in grasshopper control. USDA Tech. Bull. 793.
17. Trimnell, D. et al., (1982). Pesticide encapsulation using a starch-borate complex as wall material, J. Apply. Polym. Sci., 27:3919–3928.
18. Trimnell, D. and Shasha, B. S. (1988). Entrapment of herbicides in starch for spray applications, J. Controlled Release 7:263–268.
19. Synek, J. (1983). Formulation, development, and application of an insecticide granule, pp. 123–131. In T. M. Kaneko and N. B. Akesson [eds.], Pesticide formulations and application systems: third symposium, ASTM STP 828. American Society for Testing and Materials, Philadelphia, 1983.
20. Vander Hooven, D. I. B. (1983). Corncob granules and pelleted carriers—new, controlled, safer methods of handling pesticides, pp. 132–140. In T. M. Kaneko and N. B. Akesson [eds.] Pesticide formulations and application systems: third symposium, ASTM STP 828. American Society for Testing and Materials, Philadelphia, 1983.

21. Weissling, T. J. and Meinke, L. J. (1991). Potential of starch encapsulated semiochemical/insecticide formulations for adult corn rootworm (Coleoptera: Chrysomelidae) control. J. Econ. Entomol. 84:601–609.

22. Wing, R. E. and Otey, T. H. (1983). Determination of reaction variables for the starch xanthide encapsulation of pesticides. J. Polym. Sci. Polym. Chem. Ed. 21:121–140.

We claim:

1. A method for preparing adherent granules encapsulating a biologically active agent, the method comprising:
   a) providing a mixture of water and a volatile organic solvent selected from the group consisting of 2-propanol, ethanol, n-butyl alcohol, and 1,4-dioxane;
   b) combining said mixture with pregelatinized starch, wherein the proportion of water, solvent and pregelatinized starch is sufficient to form discrete granules, wherein said starch is selected from the group consisting of pregelatinized corn flour, pregelatinized pearl cornstarch, pregelatinized waxy cornstarch, pregelatinized potato amylopectin, and mixtures, thereof, and wherein the biologically active agent is provided as a component of the granules in an amount effective to induce the desired response in a target organism; and
   c) exposing the mixture to conditions sufficient to permit evaporation of the solvent and formation of granules comprising an effective amount of the agent encapsulated in said starch.

2. The method of claim 1, wherein said biologically active agent is selected from the group consisting of living pathogens, chemical insecticides, pest attractants, and mixtures thereof.

3. The method of claim 1 wherein the biologically active agent comprises a living pathogen of insects selected from the group consisting of bacteria, fungi, viruses, protozoa, and nematodes.

4. The method of claim 1, wherein the biologically active agent is a combination of a chemical or biological pesticide in a pesticidally effect amount and a pest attractant.

5. The method of claim 1, wherein said organic solvent is 2-propanol.

6. A product produced by the method of claim 1.

7. The method of claim 1, wherein said biologically active agent is a chemical insecticide.

8. A product produced by the method of claim 7.

9. The method of claim 1 wherein said biologically active agent is *Bacillus thuringiensis*.

10. A product produced by the method of claim 9.
11. A product produced by the method of claim 2.
12. A product produced by the method of claim 3.
13. A product produced by the method of claim 4.

* * * * *